United States Patent
Menz et al.

(10) Patent No.: US 6,764,494 B2
(45) Date of Patent: Jul. 20, 2004

(54) DEVICE FOR REMOVAL OF AN AORTA VALVE AT A HUMAN HEART IN COURSE OF A MINIMAL SURGICAL OPERATION

(75) Inventors: Wolfgang Menz, Dettenheim (DE); Andreas Schoth, Merdingen (DE)

(73) Assignees: University Hospital Centre Freiburg, Freiburg (DE); Albert-Ludwig University, Freiburg (DE)

( * ) Notice: Subject to any disclaimer, the term of this patent is extended or adjusted under 35 U.S.C. 154(b) by 0 days.

(21) Appl. No.: 09/971,687

(22) Filed: Oct. 9, 2001

(65) Prior Publication Data

US 2002/0082630 A1 Jun. 27, 2002

(30) Foreign Application Priority Data

Oct. 9, 2000 (DE) .......................................... 100 49 865

(51) Int. Cl.[7] .............................................. A61B 17/22
(52) U.S. Cl. ...................... 606/159; 606/194; 606/180
(58) Field of Search ................................ 606/159, 180, 606/79, 170, 171, 194, 200, 198; 623/1.24, 1.21, 2.16, 2.2

(56) References Cited

U.S. PATENT DOCUMENTS

| | | | | |
|---|---|---|---|---|
| 4,552,333 A | * | 11/1985 | Niemi | 251/149.9 |
| 5,100,423 A | * | 3/1992 | Fearnot | 606/159 |
| 5,250,059 A | * | 10/1993 | Andreas et al. | 606/159 |
| 5,776,153 A | * | 7/1998 | Rees | 606/159 |
| 5,855,601 A | | 1/1999 | Bessler et al. | 623/2 |
| 6,053,932 A | * | 4/2000 | Daniel et al. | 606/200 |
| 6,135,991 A | * | 10/2000 | Muni et al. | 606/159 |
| 6,290,710 B1 | * | 9/2001 | Cryer et al. | 606/200 |
| 6,299,623 B1 | * | 10/2001 | Wulfman | 606/159 |
| 6,361,545 B1 | * | 3/2002 | Macoviak et al. | 606/200 |
| 6,402,745 B1 | * | 6/2002 | Wilk | 606/41 |
| 6,491,672 B2 | * | 12/2002 | Slepian et al. | 604/267 |
| 2002/0010487 A1 | * | 1/2002 | Evans et al. | 606/180 |
| 2003/0040792 A1 | * | 2/2003 | Gabbay | 623/2.11 |

FOREIGN PATENT DOCUMENTS

| | | | |
|---|---|---|---|
| DE | 69030116 | 2/1991 | ............ A61F/2/24 |
| DE | 19907646 | 8/2000 | ............ A61F/2/24 |
| WO | 9301768 | 2/1993 | ............ A61F/2/24 |

* cited by examiner

Primary Examiner—Michael J. Milano
Assistant Examiner—Paul Roberts
(74) Attorney, Agent, or Firm—Antonelli, Terry, Stout & Kraus, LLP

(57) ABSTRACT

What is described here is a device for ablation of an aortic valve on the human heart by a minimally invasive surgical operation, comprising a centering and fixing body adapted to be introduced inside the aorta, which can be fixed relative to the aorta via at least one holding means, a drive shaft projecting centrally through said centering and fixing body, at least in part, and presenting a distal end, a cutting device fixedly mounted for rotation on the drive shaft in the region of the distal end of the drive shaft, as well as an aspiration device provided on the proximal side, relative to said cutting means, on said centering and fixing body.

22 Claims, 3 Drawing Sheets

DEVICE FOR REMOVAL OF AN AORTA VALVE AT A HUMAN HEART IN COURSE OF A MINIMAL SURGICAL OPERATION

BACKGROUND OF THE INVENTION

1. Field of the Invention

The present invention relates to a device for ablation of an artic valve on the human heart by a minimally invasive surgical operation.

2. Prior Art

The malfunctioning of an aortic valve results in cardiac insufficiency and hence in a situation that is potentially fatal for the patient. For repair of such a defect, artificial aortic valves have been developed which are implanted as a substitute for the damaged valve in complex and risky open-heart surgery (sternotomy). The operation becomes particularly difficult when there is strong calcareous degeneration on the natural valve because painstaking attention must be paid during removal in order to ensure that calcification particles will not enter the blood circulation and cause there thromboses at other sites in the body. It is common to fasten the replacement valves—which are either mere engineering products or derived from porcine valves—by suturing in the place of the removed valve.

There are numerous approaches in the development of methods simplifying this complex procedure of aortic-valve replacement in terms of both the surgical technique and the discomfort and strain for the patient, aiming at a minimally invasive technique of replacement of the aortic valve. In these approaches, the operation is performed via the femoral artery or even through the groin.

In view of the very restricted possibilities of access in the aortic arch, it is inevitable to adopt complex surgical strategies, firstly for explantation of the calcified aortic valve and secondly for implantation of an artificial valve in situ. Apart from all difficulties involved in the surgical operation—even though minimally invasive surgery is concerned that operates on advanced catheter technology—a maximum of concentration and above all a steady hand is demanded from the surgeon, specifically as the individual steps of surgical handling are within the millimetre range and therebelow. With the minimally invasive operation being performed with a sustained natural function of the heart, it is moreover important to carry out the operation as quickly as possible in order to keep the strain on the cardiac system at a minimum, which means that an operation of this kind is performed under a certain pressure in terms of time.

A special aspect is the explantation or ablation of the calcified aortic valve that must be removed completely from the aorta as quickly as possible, without lesion of adjoining unaffected tissue regions, specifically as the explantation involves mostly the application of mechanically acute cutting tools. Furthermore, it is important to ensure that severed tissue fragments or calcification particles will be extracted from the blood stream without any residues so as to avoid the occurrence of embolism or thromboses.

SUMMARY OF THE INVENTION

The present invention is based on the task of solving the problem configuring a device for ablation of an aortic valve on the human heart by a minimally invasive surgical operation in such a way that the ablation of the calcified valve will be performed rapidly, without any residues and without excessive strain on the surrounding tissue material. It should become possible to collect severed calcification particles or freely movable tissue fragments completely or to extract them from the blood stream, respectively, by means of the device. In particular, the device should allow the removal of the valve while the natural cardiac action is sustained.

In accordance with the present invention a device for ablation of the aortic valve on the human heart by a minimally invasive surgical operation is configured to comprise a centering and fixing body adapted to be introduced inside the aorta, which body can be fixed, relative to the aorta, via at least one holding means. A drive shaft projecting through the centering and fixing body in a central position, at least partly, comprises a distal end on whose distal terminal section a cutting means is fixed for rotation. Moreover, on the centering and fixing body, on the proximal side relative to the cutting means, an aspirator means is provided through which the blood present in the aorta as well as calcification particles detached by the process of severing the calcified aortic valve may be extracted from the blood stream.

The centering and fixing body, which is preferably configured in the form of a hollow cylinder, comprises holding means that serve for fixing the centering and fixing body inside the aorta at an invariably defined location. The holding means are preferably designed as dilatable volume elements in the form of balloons or holding webs spreadable away from the cylinder, which are mounted on the outside cylinder wall. In this manner, it is possible that the centering and fixing body remains automatically stationary inside the aorta.

A particularly preferred embodiment provides for a fixedly implanted operating structure for positioning the centering and fixing body inside the aorta, which structure conforms to the inner wall of the aorta at a suitable location—for example at a point adjacent to the aortic valve to be ablated—in a stationary manner. The operating structure in its turn comprises a bayonet catch for a detachable fixed connection, into which the correspondingly shaped counter-contour of the bayonet catch can be inserted on the centering and fixing body. The operating structure, which will not be discussed here in further details, serves as a topologic fixing point for both the invention and further surgical tools, specifically catheter tools.

The inventive device for the selective ablation of the aortic valve will be explained in more details in the following, with reference to the figures described hereinbelow.

BRIEF DESCRIPTION OF THE DRAWINGS

The following is an exemplary description of the present invention by embodiments, without any limitation of the general inventive idea, with reference to the drawing wherein.

DESCRIPTION OF THE PREFERRED EMBODIMENTS

Figure 1:
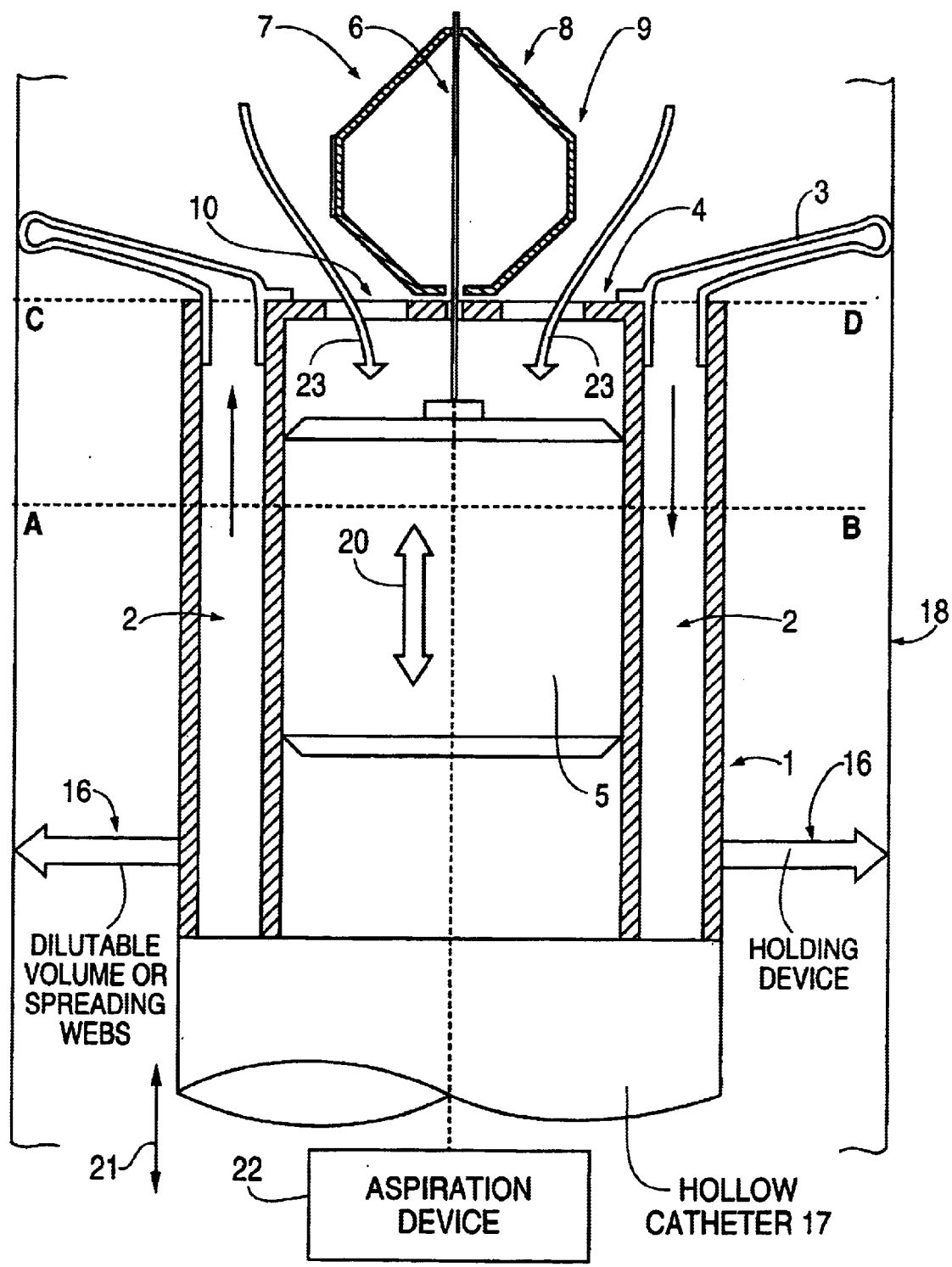
FIG. 1 is a cross-sectional view taken through an embodiment of the inventive design.

FIG. 1 shows a cross-sectional view taken through the device of the inventive design, including a centering and fixing body configured in the form of a cylinder 1. In a direction towards the proximal side (i.e. towards the bottom of FIG. 1) the cylinder 1 is fixedly connected to a hollow catheter 17 in a fluid-tight manner for detachment. On two opposing lateral wall regions inside the cylinder 1 two feeder or discharge lines 2, respectively, are provided that open into elastically deformable cardiac valves 3 of a membrane like design on the distal side of the cylinder 1 which expand to engage the aorta wall 18 to block aorta blood flow past the valves and which contract to permit aortic blood flow past the valves. The elastically designed artificial cardiac valves 3 peripherally enclose the upper section of the cylinder 1 (explained in detail in the following) which is provided with a cover plate 4. The function of the artificial cardiac valves 3 will be discussed in more detail below. The cylinder 1 is held in place by a holding device 16 which may be a dilatable volume or holding web which spreads away from the cylinder to engage the wall 18 of the aorta. Also a sleeve (not illustrated) may be positioned on the wall 18 having a bayonet catch (not illustrated) to which a bayonet catch (not illustrated) mounted on the fixing device can be fixedly joined.

Inside the cylinder 1, an electric motor 5 is connected to a drive shaft 6, with the drive shaft 6 projecting through the cover plate 4 on the distal side. A cutting device 7 is fixedly disposed for rotation on the distal side drive shaft 6 region, which device consists of two coherent supporting elements 8 in the illustrated embodiment. The supporting elements 8 are stationarily connected to the distal end of the drive shaft whereas their end on the proximal side is configured for longitudinal movement relative to the drive shaft 6. Cutting elements 9 are provided centrally relative to the supporting elements 8, which cutting elements create a cutting effect on the surrounding tissue, in response to an appropriate sense of rotation, in such a way that the tissue will be cut out in the form of a circular ring by the rotating movement of the cutting elements 9.

The electric motor 5 is mounted for longitudinal movement 20 relative to the longitudinal axis of the cylinder so that the drive shaft can be shifted by the cover plate 4 towards the distal and proximal sides. When the electric motor 5 is shifted in the proximal direction, the supporting elements 8 are urged against the cover plate 4 while the cutting device 7 is spread. Depending on the position of the electric motor 5 inside the cylinder 1 and, as a consequence, depending on the spreading of the supporting elements 8, it is possible that with a corresponding rotation of the cutting elements 9 apertures of different diameters are cut from a tissue region, for example from a calcified cardiac valve. Moreover, the cover plate 4 provides for openings 10 through which the blood above the cover plate may enter the interior of the cylinder 1 through at least one passage 23 from where it can be passed in a proximal direction through an appropriate hollow catheter 17 for discharge from the body under suction provided by an aspiration device 22 located outside the patent's body.

Figure 2A:
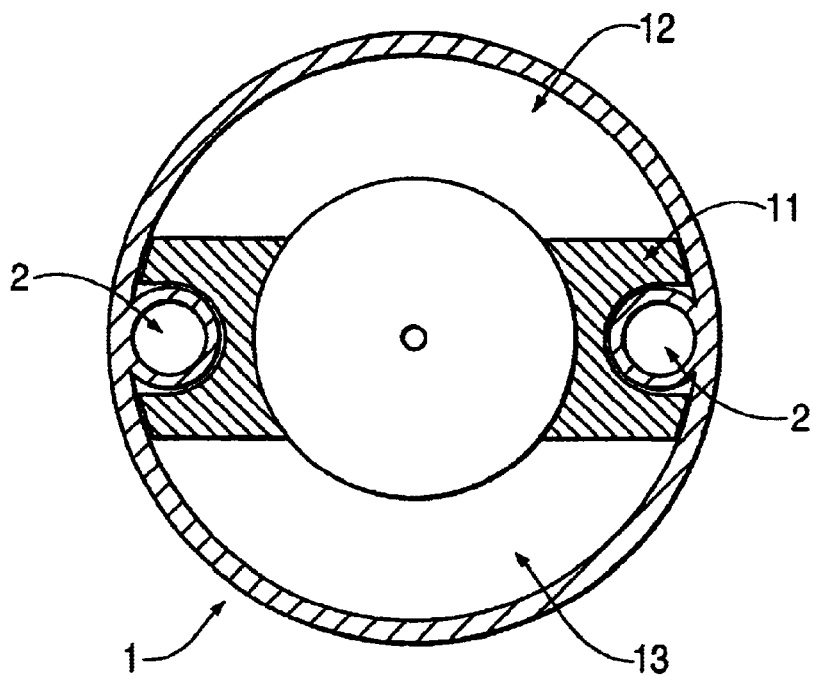
FIGS. 2a and b are each sectional views in correspondence with the sectional planes indicated in FIG. 1; as well as FIGS. 3a, b, c and d represent the elastically insufflatable aortic valve membrane for maintaining the natural cardiac rhythm.

The sectional view illustrated in FIG. 2a corresponds to the linear section according to the line A–B in FIG. 1. In FIG. 2a, the two feeder or discharge lines 2 can be seen that oppose each other inside the cylinder 1. Moreover, a spacer element 11 ensures the central positioning of the electric motor 5 inside the cylinder 1. The blood that has entered the interior of the cylinder 1 through the at least one passage 23 can flow out to the proximal side through the regions 12 and 13.

Figure 2B:
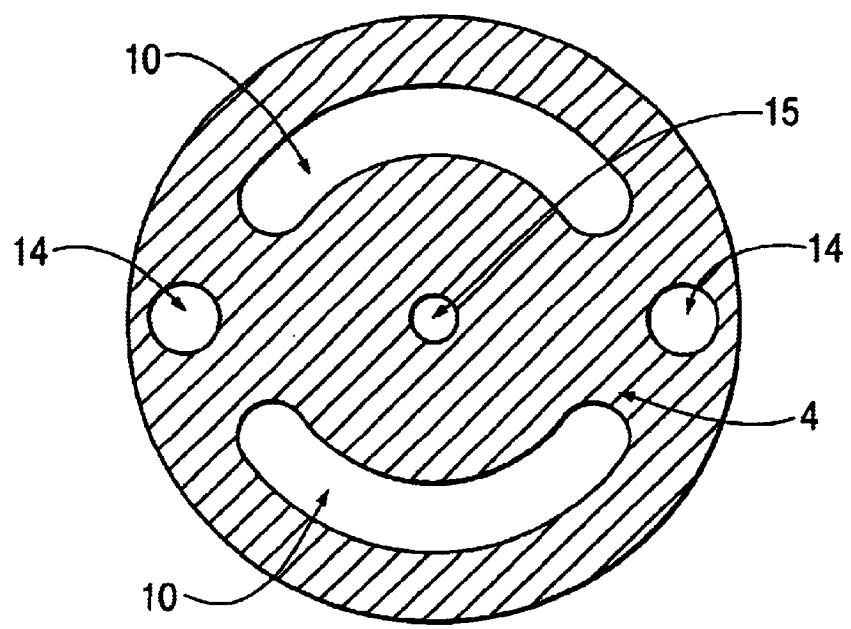

FIG. 2b illustrates a sectional view in correspondence with the linear section C–D according to FIG. 1 and shows substantially the structure of the cover plate 4. The two openings 10 are provided in the cover plate 4, which are oriented in registry with the regions 12 and 13. Furthermore, openings 14 are provided which correspond to the feeder or discharge lines 2, respectively. An opening 15 is provided centrally relative to the opening 15 through which the drive shaft 6 of the motor 5 is passed.

Figure 3A:
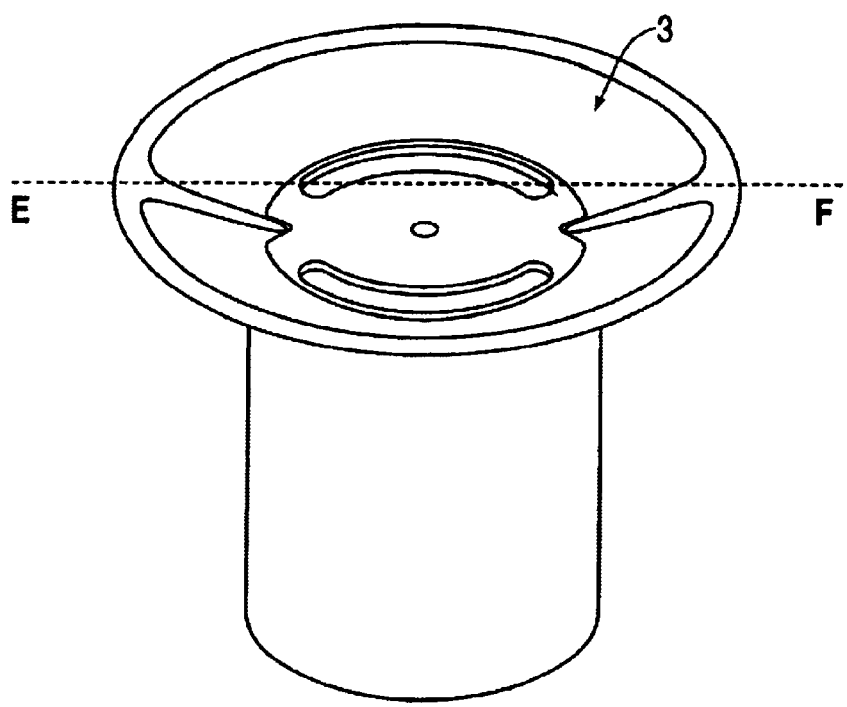
Figure 3B:
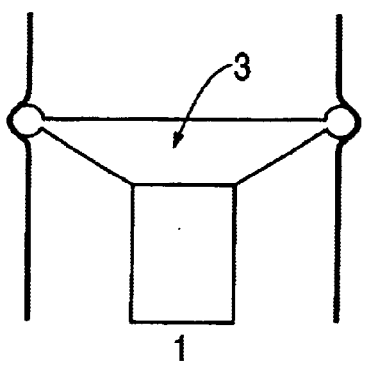
Figure 3C:
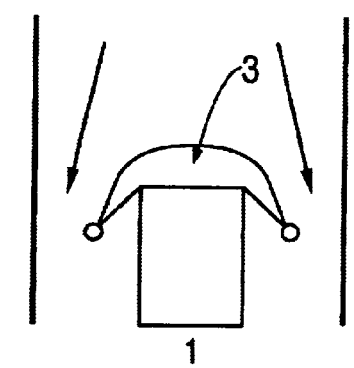
Figure 3D:
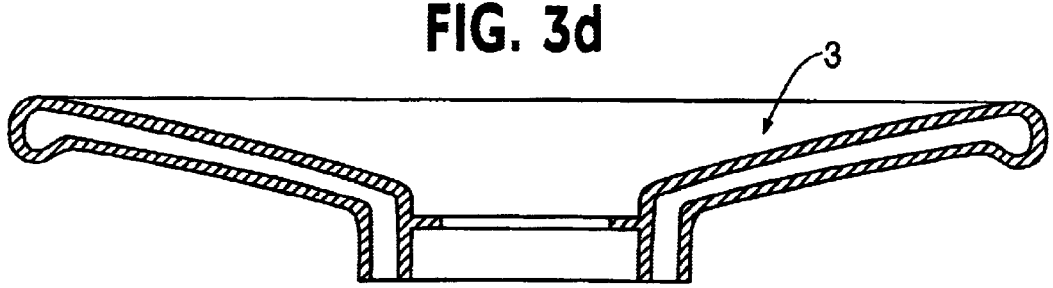

FIG. 3a is a perspective view of the insulated artificial cardiac valve element 3 that is mounted on the distal side on the cylinder 1. In correspondence with FIG. 3b, the artificial valve 3 ensures that in the insufflated, that is in the inflated, condition it will establish a fluid-tight sealing against the aorta wall 18. Due to the insufflated condition of the artificial cardiac valve 3, the natural blood stream is discontinued. When the artificial cardiac valve 3 is deflated the natural blood stream can flow through the aorta without being obstructed, by passing along the cylinder 1, as is shown in FIG. 3c. FIG. 3b shows a sectional view of the artificial cardiac valve 3 with details of the structure.

The following is a detailed description of the mode of operation of the inventive device.

The presence of the holding structure 16—which may be fixed and implanted already in the aortic arch and serve as a topologically fixed supporting means—is an expedient for the minimally invasive surgical operation for ablation of a calcified aortic valve. The operating structure provides in particular for a detachable fixed bayonet catch means which engages an appropriately configured counter-holding means provided on the cylinder 1 of the afore-explained device on the outer wall of the cylinder. The holding structure 16, which may be designed as bayonet catch (not illustrated, may be mounted on the outer wall of the cylinder.

The surgical device configured in the form illustrated in FIG. 1 is inserted into the interior of the operating structure and appropriately fixed with the holding structure 16. The cylinder 1 is positioned relative to the cardiac valve to be ablated in such a way that the cutting device 7 projects into the zone of the cardiac valve to be ablated. When the electric motor 5 turns in the corresponding sense of rotation the cutting elements 9 are equally caused to rotate, so that a circular hole can be cut out from the calcified tissue. When the motor 5 is retracted inside the cylinder 1 in a proximal direction the supporting elements 8 are spread and hence the cutting diameter is enlarged. In this manner, a cardiac valve can be radially exfoliated from the inside towards the outside by means of the cutting elements. During the surgical operation the artificial resilient cardiac valve 3, which is preferably made of an elastomer material, assumes the valve function. When the artificial cardiac valve 3 is in its deflated condition the blood flows between the outer walls of the cylinder and the tissue wall of the aorta. When the cardiac valve 3 is pressurised through the feeder line 2 and by the ribs of the elastomer material the membrane of the artificial cardiac valve is spread and seals itself against the tissue wall 18 of the aorta. The blood stream is hence stopped. The function of the artificial aortic valve 3 is externally controlled from the outside. The pressure in the heart, the potential of the sino-atrial node or any other physiological signal may be used as control signal. With this concept, an optional adjustment of the closing interval of the artificial cardiac valve 3 is possible for surgical reasons, for instance, the valve may also be held in the closed condition over one or several periods.

A defective natural cardiac valve is ablated as follows:

After the cylinder 1 has been axially positioned as represented by arrow 21 adjacent to the aortic valve (not illustrated) by the holding device 16, the aortic valve to be removed is dilated in the manner explained above, using the drive shaft 6 and the cutting elements 9. At the same time, the artificial cardiac valve 3 is pressurized to seal automatically against the aorta wall 18. Then the drive shaft is caused to rotate and the cutting device 7 with the cutting elements 9 exfoliates the aortic valve from the inside. During the closing period of the artificial cardiac valve 3, the blood, together with the removed material, is pumped through the aspiration opening 10 out of the body under suction provided by the aspiration device 22 through the catheter 17. The blood can then be cleaned by removal of particles and subjected to an appropriate processing operation outside the body. When there are no longer any particles in the aorta, the artificial cardiac valve 3 may be opened and closed in correspondence with the pulse rhythm. After a recovery pause the artificial cardiac valve 3 is closed again and a new processing cycle is carried out. In this step, the motor 5 is retracted in the proximal direction as indicated by arrow 20 by retraction of connector (not illustrated) extending outside the patents body so that the cutting device spreads and that the ablation of the natural valve can be continued. These cycles are repeated several times until the aortic valve has been removed to a sufficient extent. Then the entire device 1 can be appropriately freed from engagement of the aorta wall 18 by retraction of the holding device 16 and removed from the body again. The application for a permanent artificial valve must subsequently be performed directly with further surgical instruments, using an appropriate operating structure.

| LIST OF REFERENCE NUMERALS | | |
|---|---|---|
| 1. | | cylinder |
| 2. | | feeder or discharge lines |
| 3. | | artificial valve, membrane |
| 4. | | cover plate |
| 5. | | electric motor |
| 6. | | drive shaft |
| 7. | | cutting device |
| 8. | | supporting element |
| 9. | | cutting element |
| 10. | | opening in the cover plate |
| 11. | | positioning frame |
| 12. and 13 | | discharge regions |
| 14. | | opening |
| 15. | | opening |

What is claimed is:

1. A device for ablation of an aortic valve of a human heart by a minimally invasive surgical operation, comprising:

a body having distal and proximal ends which is for introduction inside the aorta, the body being for fixing relative to the aorta by at least one holding device which is attached to the body and which is for engaging the aorta;

a drive shaft, projecting centrally at least in part through the body and outside of the distal end;

a cutting device fixedly mounted for rotation on the drive shaft in a region outside of the distal end for abating the aortic valve; and an aspiration device for aspirating debris from cutting of the aortic valve through at least one passage in the body facing the aorta, and disposed radially outward from the drive shaft, extending through the body and a catheter for fluid communication with the proximal end and the aspiration device for aspirating debris in aortic blood of a patient resultant from ablation of the aortic valve, and wherein the body is a hollow cylinder for attachment to a distal end of the catheter while inside the patient and comprises an electric motor from which projects the drive shaft that extends through the hollow cylinder and through a cover plate at the distal end connected to the hollow cylinder.

2. A device according to claim 1, wherein:

the body is a cylinder having a wall and the at least one passage is disposed inside the wall and the at least one passage is for connecting the flow of blood and debris from a volume inside the aortia between the aortic valve and the distal end of the body to the catheter.

3. A device according to claim 2, wherein:

the cylinder has a wall on which the holding device is provided and the holding device is one of a dilatable volume element or holding webs which spread away from the cylinder.

4. A device according to claim 3, wherein:

the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and is slideably connected to the drive shaft at a second location located closer to the distal end of the drive shaft.

5. A device according to claim 1, wherein:

the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and is slideably connected to the drive shaft at a second location located closer to the distal end of the drive shaft.

6. A device according to claim 2, wherein:

the body is a hollow cylinder, attached to a distal end of the catheter, through which the drive shaft extends and projects through a cover plate that is connected to the hollow cylinder at the distal end.

7. A device according to claim 6, wherein:

at least one opening is provided in the cover plate which is coupled to the at least one passage extending through the body which is coupled to the aspiration device by the catheter through which the debris and aortic blood pass.

8. A device according to claim 3, wherein:

the body is a hollow cylinder, attached to a distal end of the catheter, through which the drive shaft extends and projects through a cover plate that is connected to the hollow cylinder at the distal end.

9. A device according to claim 8, wherein:

at least one opening is provided in the cover plate which is coupled to the at least one passage extending through the body which is coupled to the aspiration device by the catheter through which the debris and aortic blood pass.

10. A device according to claim 6, wherein:

at least one radially extending inflatable artificial cardiac valve that when inflated extends from the body and bears in a fluid-tight manner against an inside wall of the aorta and can be spaced from the wall of the aorta in a deflated condition.

11. A device according to claim 7, wherein:
at least one radially extending inflatable artificial cardiac valve that when inflated extends from the body and bears in a fluid-tight manner against an inside wall of the aorta and can be spaced from the wall of the aorta in a deflated condition.

12. A device according to claim 8, wherein:
at least one radially extending inflatable artificial cardiac valve that when inflated extends from the body and bears in a fluid-tight manner against an inside wall of the aorta and can be spaced from the wall of the aorta in a deflated condition.

13. A device according to claim 9, wherein:
at least one radially extending inflatable artificial cardiac valve that when inflated extends from the body and bears in a fluid-tight manner against an inside wall of the aorta and can be spaced from the wall of the aorta in a deflated condition.

14. A device according to claim 6, wherein:
the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and is slideably connected to the drive shaft at a second location located closer to the distal end of the drive shaft.

15. A device according to claim 5, wherein:
the drive shaft is supported for longitudinal movement relative to the cover plate such that the supporting elements of the cutter are spreadable resultant from longitudinal movement relative to the cover plate which causes radial movement of the cutting elements dependent upon the direction of the longitudinal movement.

16. A device according to claim 15, wherein:
at least one opening is provided in the cover plate which is coupled to the at least one passage extending through the body which is coupled to the aspiration device by the catheter through which the debris and aortic blood pass.

17. A device according to claim 16, comprising:
at least one radially extending inflatable artificial cardiac valve that when inflated extends from the body and is for bearing in a fluid-tight manner against an inside wall of the aorta and can be spaced from the wall of the aorta in a deflated condition.

18. A device according to claim 17, wherein:
at least one duct is provided inside the body, through which at least one inflatable artifical cardiac valve connected to the body, including a resilient membrane, is inflated and deflated again.

19. A device according to claim 16, wherein:
the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and is slideably connected to the drive shaft at a second location located closer to the distal end of the drive shaft.

20. A device according to claim 18, wherein:
the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and slideably connected to the drive shaft at a second location located closer to the distal end of the drive shaft.

21. A device for ablation of an aortic valve of a human heart by a minimally invasive surgical operation, comprising:
a body having distal and proximal ends which is for introduction inside the aorta, the body being for fixing relative to the aorta by at least one holding device which is attached to the body and which is for engaging the aorta;
a drive shaft, projecting centrally at least in part through the body and outside of the distal end;
a cutting device fixedly mounted for rotation on the drive shaft in a region outside of the distal end for abating the aortic valve; and
an aspiration device for aspirating debris from cutting of the aortic valve through at least one passage in the body facing the aorta, and disposed radially outward from the drive shaft, extending through the body and a catheter for fluid communication with the proximal end and the aspiration device for aspirating debris in aortic blood of a patient resultant from ablation of the aortic valve; and wherein
the body is a hollow cylinder, attached to a distal end of the catheter, through which the drive shaft extends and projects through a cover plate that is connected to the hollow cylindrical at the distal end.

22. A device for ablation of an aortic valve of a human heart by a minimally invasive surgical operation, comprising:
a body having distal and proximal ends which is for introduction inside the aorta, the body being for fixing relative to the aorta by at least one holding device which is attached to the body and which is for engaging the aorta;
a drive shaft, projecting centrally at least in part through the body and outside of the distal end;
a cutting device fixedly mounted for rotation on the drive shaft in a region outside of the distal end for abating the aortic valve; and
an aspiration device for aspirating debris from cutting of the aortic valve through at least one passage in the body facing the aorta, and disposed radially outward from the drive shaft, extending through the body and a catheter for fluid communication with the proximal end and the aspiration device for aspirating debris in aortic blood of a patient resultant from ablation of the aortic valve; and wherein
the cutting device comprises at least two cutting tools disposed in symmetry relative to the drive shaft, with each cutting tool being provided with a supporting element which is deformed in the longitudinal direction relative to the drive shaft to vary a cutting radius of the cutting tool and is fixedly connected on a distal end of the drive shaft and is slideably connected to the drive shaft at a second location located closer to the distal end of the drive shaft.

\* \* \* \* \*